US 7,247,859 B2

(12) United States Patent
Murphy et al.

(10) Patent No.: US 7,247,859 B2
(45) Date of Patent: Jul. 24, 2007

(54) SYSTEMS, METHODS AND APPARATUS FOR A REFERENCE DISPLAY OF A DIGITAL IMAGE DETECTOR

(76) Inventors: Lawrence Elwood Murphy, 3839 N. Murray Ave., Shorewood, WI (US) 53211; Habib Vafi, 19260 Baythorn Way, Brookfield, WI (US) 53045

( * ) Notice: Subject to any disclaimer, the term of this patent is extended or adjusted under 35 U.S.C. 154(b) by 175 days.

(21) Appl. No.: 10/998,082

(22) Filed: Nov. 26, 2004

(65) Prior Publication Data

US 2006/0113481 A1 Jun. 1, 2006

(51) Int. Cl.
*G01T 1/24* (2006.01)
*H04N 5/222* (2006.01)
(52) U.S. Cl. .............................. 250/370.09; 348/333.07
(58) Field of Classification Search ........... 250/370.09; 348/333.07
See application file for complete search history.

(56) References Cited

U.S. PATENT DOCUMENTS

| 4,706,117 | A | * | 11/1987 | Schoolman | 348/53 |
| 4,837,817 | A | * | 6/1989 | Maemori | 348/211.4 |
| 5,288,977 | A | * | 2/1994 | Amendolia et al. | 235/375 |
| 6,906,330 | B2 | * | 6/2005 | Blevis et al. | 250/370.09 |
| 2002/0050986 | A1 | * | 5/2002 | Inoue et al. | 345/204 |
| 2004/0188625 | A1 | * | 9/2004 | Schulze-Ganzlin | 250/370.09 |

* cited by examiner

*Primary Examiner*—David Porta
*Assistant Examiner*—Mindy Vu
(74) *Attorney, Agent, or Firm*—Carl Horton; Peter Vogel; Michael Smith (57) ABSTRACT

Systems, methods and apparatus are provided through which in some embodiments a reference display receives reference information and displays the reference information from a digital image detector, wherein the reference display is in close proximity to the digital image detector.

38 Claims, 11 Drawing Sheets

SYSTEMS, METHODS AND APPARATUS FOR A REFERENCE DISPLAY OF A DIGITAL IMAGE DETECTOR

FIELD OF THE INVENTION

This invention relates generally to digital image detectors, and more particularly to visual displays of images of the digital image detectors.

BACKGROUND OF THE INVENTION

In conventional imaging apparatus, a subject of an imaging procedure is imaged by an X-ray beam from an X-ray source. An X-ray image is captured by an imaging receptor. The imaging receptor may be a film-based receptor, or increasingly so, a digital image receptor. The source and the imaging receptor are located in a room often referred to as an "imaging room."

In these conventional imaging systems, an imaging console is located outside the imaging room. The imaging console includes a visual display of information describing the imaging procedure.

The information displayed on the visual display of the imaging console is reviewed by an operator of the imaging system after the imaging procedure is complete. The information is reviewed to determine the quality of the image. If the image is not of acceptable quality, the image procedure is repeated.

A human subject of the imaging procedure often feel puzzled, confused and in a quandary about the success of the imaging procedure because the human subject does not have access to the information on the visual display of the imaging console. In a society that increasingly values access to information, some human subjects feel very out-of-place when they have no direct access to information on the imaging procedure that could have a big effect on their life. This lack of information sometimes leads the human subject a feeling that the imaging procedure is somewhat mysterious, and in turn leads the human subject to a lack of confidence on the success of the imaging procedure.

In regards to digital image receptors, the digital image receptors weigh less than ten pounds and thus are fairly easy to move around. The portability of the digital image receptors is a very helpful and useful attribute of the digital image receptors, but the portability also has the effect of bringing the digital image receptors with contact with more objects. Contact with other objects can result in damage to the exterior housing of the digital image receptors.

For the reasons stated above, and for other reasons stated below which will become apparent to those skilled in the art upon reading and understanding the present specification, there is a need in the art for improved access to the imaging information by the operator in order to reduce the time of completing the imaging procedure. There is also a need for improved access to the imaging information by a human subject of the imaging procedure in order to reduce the mysteriousness of the imaging procedure and improve the confidence of the human subject in the success of the imaging procedure. In addition, there is a need to protect the exterior housing of digital image receptors from damage by contact from other objects.

BRIEF DESCRIPTION OF THE INVENTION

The above-mentioned shortcomings, disadvantages and problems are addressed herein, which will be understood by reading and studying the following specification.

In one aspect, a medical digital image detector is operably coupled to a display that can be readily located in the same room as the digital image. The ability to readily locate the reference display in the same room as the digital image detector provides improved access to the imaging information by the operator which in turn reduces the time of completing the imaging procedure. The ability to readily locate the reference display in the same room as the digital image detector also improves access to the imaging information by a human subject of the imaging procedure which in turn demystifies the imaging procedure and improves the confidence of the human subject in the success of the imaging procedure.

In another aspect, the reference display is smaller than the conventional computer monitor. In yet another aspect, the display has a height and a width of approximately three inches by three inches.

In still yet a further aspect, a radiolucent sleeve provides mechanical protection to the housing of a digital image detector, and particularly the digital image receptor, while allowing X-ray photons to pass through to the digital image receptor. Thus, a digital image detector can be operated while the digital image detector is in the radiolucent sleeve.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into five sections. In the first section, a system level overview is described. In the second section, apparatus of embodiments are described. In the third section, methods of embodiments are described. In the fourth section, the hardware and the operating environment in conjunction with which embodiments may be practiced are described. Finally, in the fifth section, a conclusion of the detailed description is provided.

System Level Overview

Figure 1:
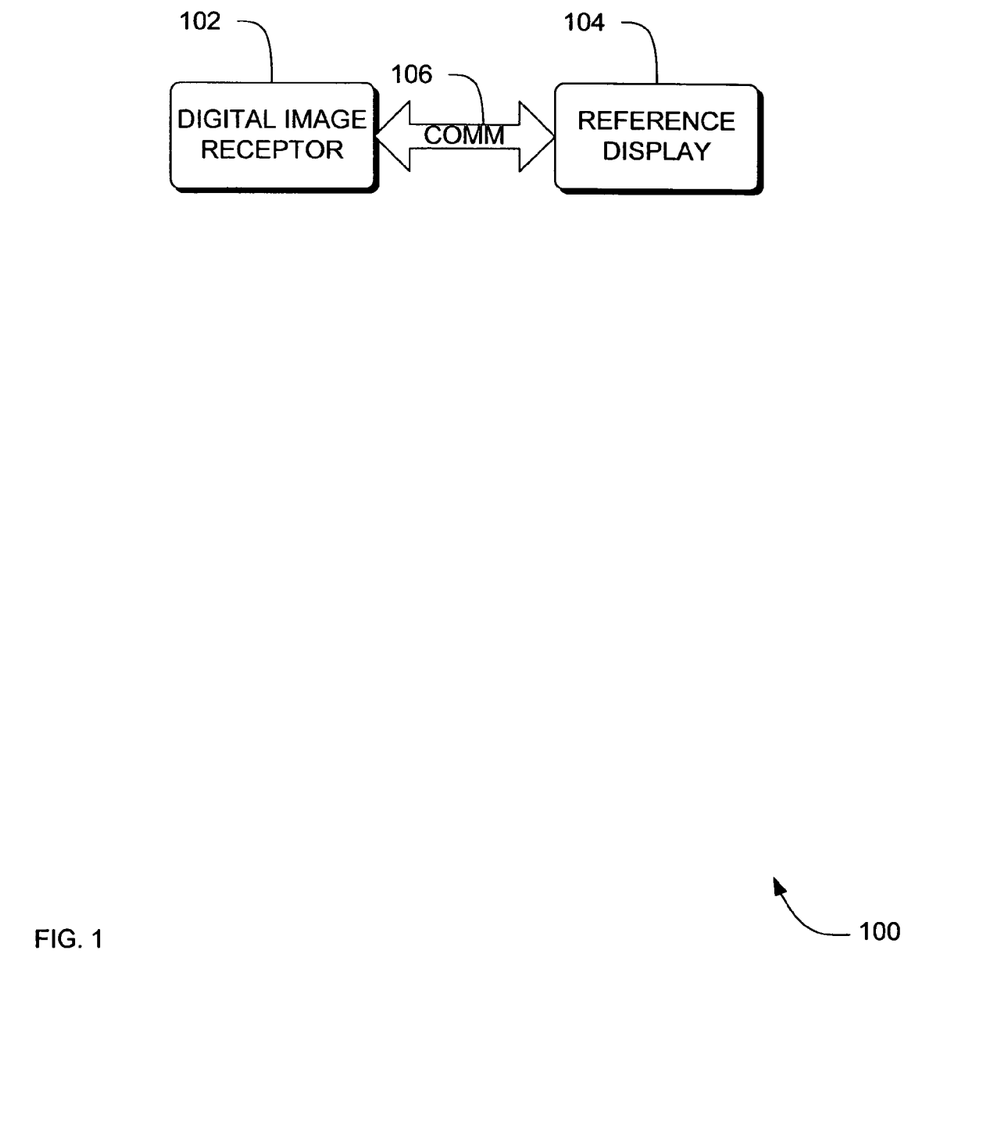
FIG. 1 is a block diagram that provides a system level overview of an apparatus to image a subject while providing a means to conveniently review an image of the subject.

FIG. 1 is a block diagram that provides a system level overview of an apparatus 100 to image a subject while providing a means to conveniently review an image of the subject. System 100 solves the need in the art for improved access to the imaging information by the operator in order to reduce the time of completing the imaging procedure. System 100 also solves the need in the art for improved access to the imaging information by a human subject of the imaging procedure in order to reduce the mysteriousness of the imaging procedure and improve the confidence of the human subject in the success of the imaging procedure.

System 100 includes a digital image receptor 102, such as an X-ray digital image detector. System 102 also includes a reference display 104 that is operably coupled through an electronic communication path 106 to the digital image receptor 102. The reference display 104 is operable to be located in the same room as the digital image receptor 102. For example, in one embodiment shown in FIG. 2, the reference display 104 is display fixedly mounted in the digital image receptor 102. In another example shown in FIG. 3, the reference display 104 is removably mounted in the digital image detector. In yet another example shown in FIG. 4, the reference display 104 is operably coupled to the digital image receptor 102 through a wireless communication path.

Figure 5:
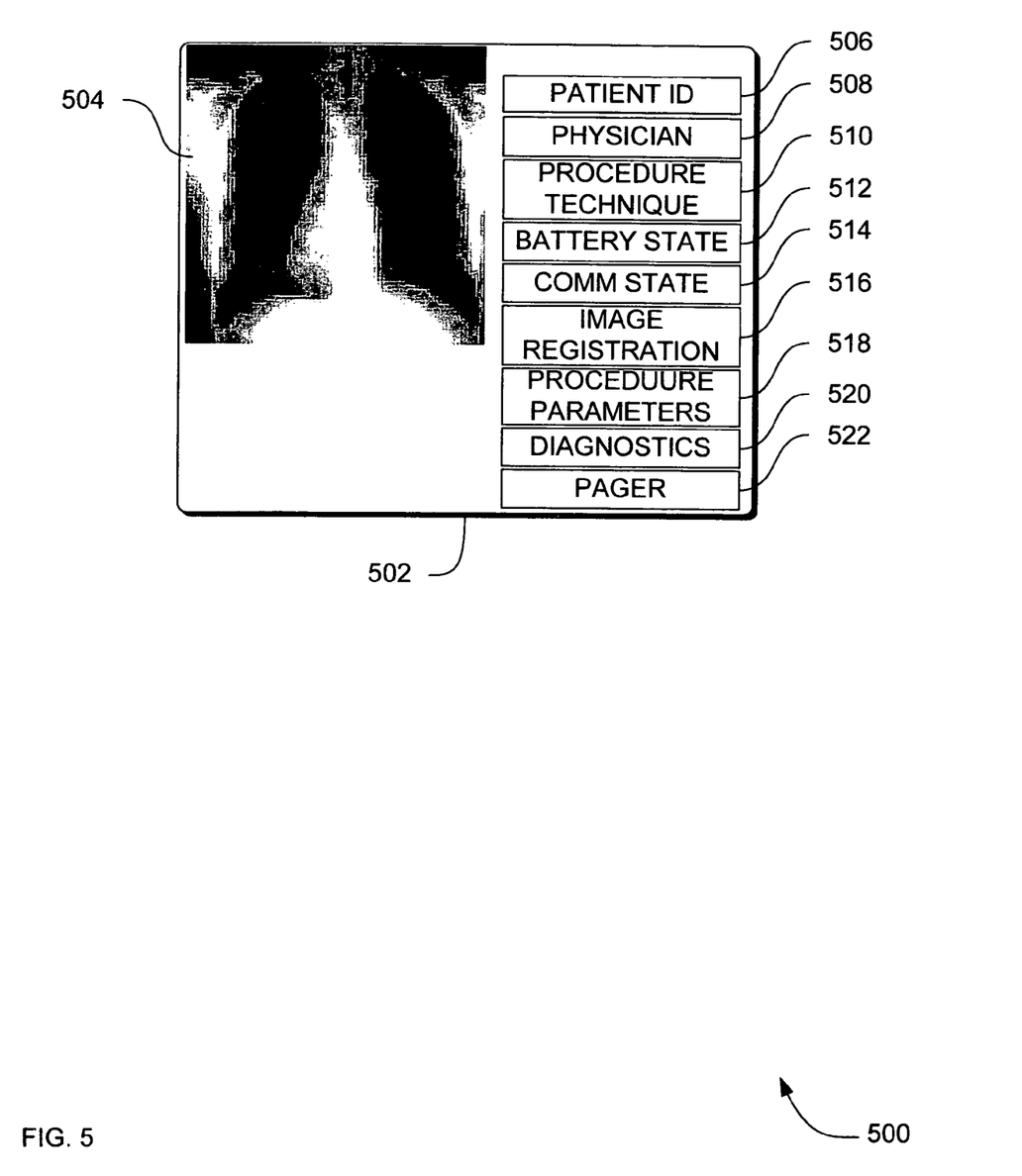
FIG. 5 is a diagram of a reference display according to an embodiment.

The reference display 104 receives signals representing reference information from the digital image receptor 102. In some embodiments, the signals are received from a microprocessor (not shown) in system 100. One embodiment of the reference display 104 is shown in FIG. 5 below.

The close proximity of the reference display 104 to the situs of imaging by the digital image receptor 102 provides for ready, quick and convenient access to the reference information by both a human subject of the imaging and by an operator of the apparatus 100. The ready, quick and convenient access to the reference information by the operator allows the operator to more conveniently review the quality of the image and anatomical alignment of the human subject, and thereafter make adjustments in the positioning of the human subject and adjustment in the parameters of the imaging procedure, thus improving quality control of the imaging procedure and reducing the number of retakes of the image.

The ready, quick and convenient access to the reference information by the subject of the imaging procedure also demystifies the imaging procedure by allowing the human subject to see the information in the reference display 104, which provides more information on the imaging procedure to the human subject, and thereby increasing the subject's confidence level in the imaging procedure.

The improving the confidence of the human subject is particularly helpful when the imaging procedure is a medical imaging procedure. The improved confidence of the human subject has a large number of benefits, such as improving confidence in the medical diagnosis procedure and possible later treatment, which reduces the likelihood that diagnosing physicians and treating physicians will be sued for medical malpractice. The improved confidence of the human subject may also improve the psychological perspective of the human subject, which may have the effect of improving the medical recovery of a diseased or injured human subject.

In some embodiments, the system 100 is a medical digital image detector. In some embodiments, the digital image receptor 102 comprises a solid state radiation detector that includes a layer of a photoconductive material characterized by a change in conductance between opposed boundaries of the layer responsive to changes in incident radiation flux. In some embodiments a layer of X-ray photoconductor is sandwiched between electrodes for conversion of X-radiation to an electrical signal.

While the system 100 is not limited to any particular digital image receptor 102, reference display 104 and electronic communication path 106, for sake of clarity a simplified digital image receptor 102, reference display 104 and electronic communication path 106 are described.

Apparatus of an Embodiment

In the previous section, a system level overview of the operation of an embodiment was described. In this section, the particular apparatus of such an embodiment are described by reference to a series of diagrams.

Figure 2:
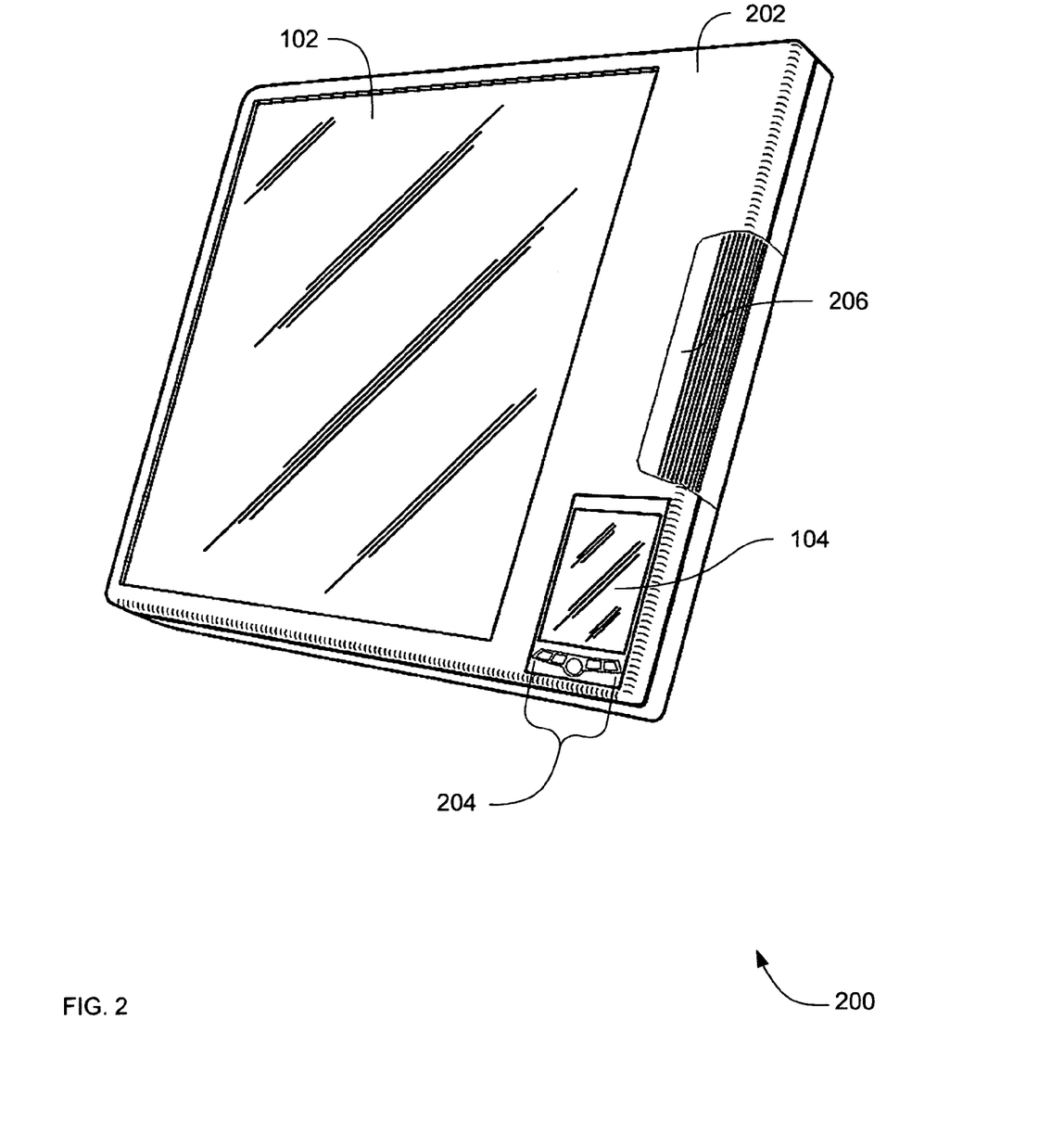
FIG. 2 is a diagram of apparatus according to an embodiment in which a reference display is integrated within a digital image detector.

FIG. 2 is a diagram of apparatus 200 according to an embodiment in which a reference display is integrated within a digital image detector. Apparatus 200 includes a housing 202. A digital image receptor 102 is mounted in a recess of the housing 202.

Apparatus 200 also includes a reference display 104 mounted in the housing 202. The reference display 104 mounted in the housing 202 of the apparatus 200 provides for a permanent, fixed close proximity of the reference display 104 to the situs of imaging by the digital image receptor 102, which in turn provides for ready access to a reference image by both a human subject of the imaging and an by operator of the apparatus 200.

In some embodiments, the apparatus 200 also includes status lights 204, such as LED lights that provide more information to the operator of the apparatus 200, which improves the ability of the operator to determine if an image received by the digital image receptor 102 is of acceptable quality. In some embodiments, apparatus 200 also includes a grip 206 for improved handling of the apparatus 200.

In some embodiments, apparatus 200 also includes a radiopaque cover (not shown) attached to the apparatus that is moveable over the reference display 102 that protects the reference display from mechanical damage and from electromagnetic damage. In some embodiments, the radiopaque cover is a leaded polycarbonate lens.

Figure 3:
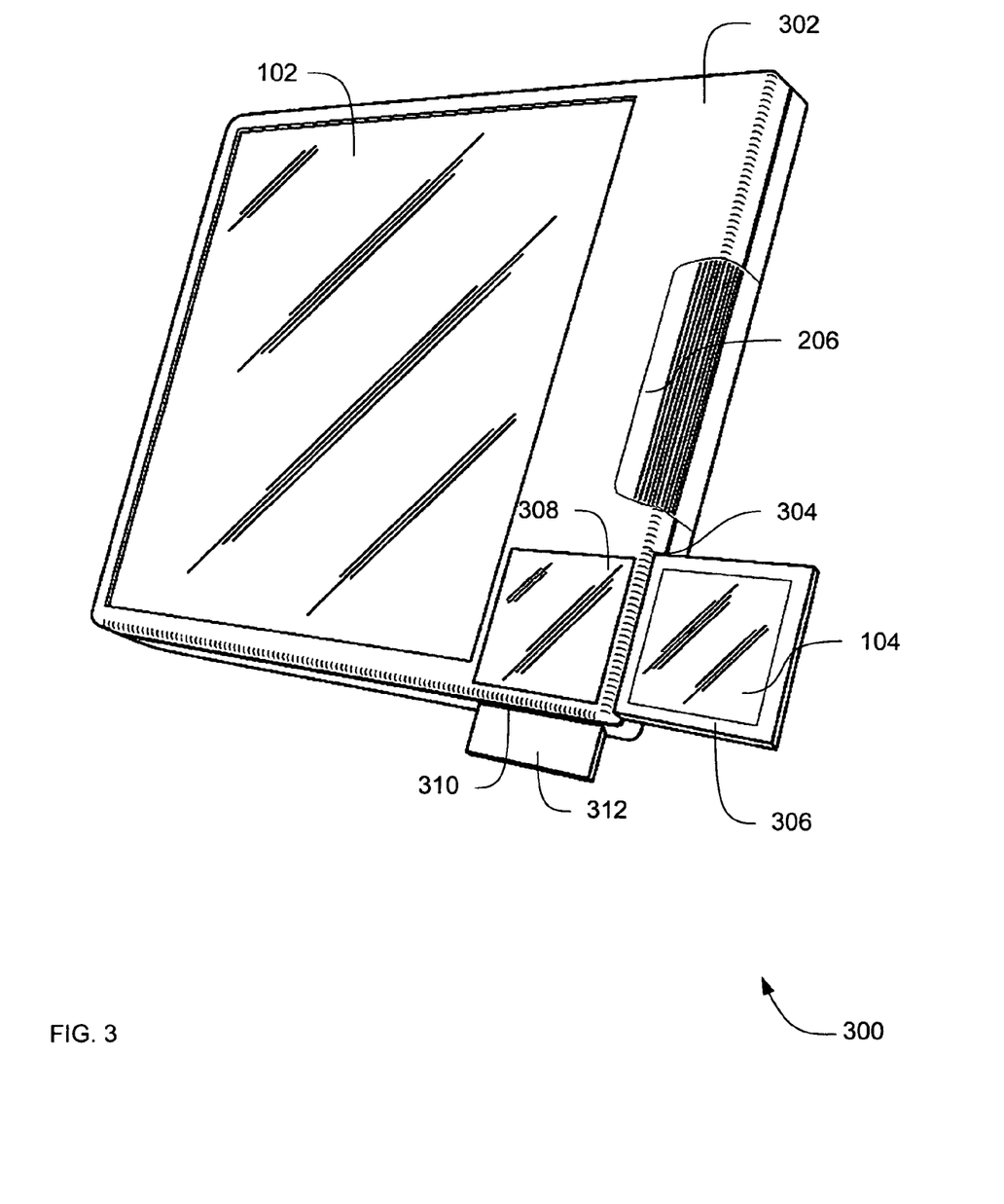
FIG. 3 is a diagram of apparatus according to an embodiment in which a reference display 104 is removably mounted in a digital image detector.

FIG. 3 is a diagram of apparatus 300 according to an embodiment in which a reference display 104 is removably mounted in a digital image detector.

Apparatus 300 includes a housing 302 comprising a recess 304. The recess 304 has inner dimensions suitable to receive a display apparatus 306. The display apparatus 306 includes reference display 104 and is a separate apparatus from apparatus 300. In some embodiments, the display apparatus 306 is an IPAQ manufactured by Hewlett Packard Company of Palo Alto, Calif.

In some embodiments, apparatus 300 includes a translucent window 308. The translucent window 308 is located over a recess (not shown) in the housing 302 that is located over a position of the reference display 104 when the display apparatus 306 is inserted in the recess 304 in housing 302. The translucent window 308 protects the front face of the display apparatus 306 when the display apparatus 306 is inserted in the recess 304 in housing 302.

In some embodiments, apparatus 300 also includes a radiopaque cover (not shown) attached to the apparatus 300 that is moveable over the recess (not shown) in the housing 302 that is located over a position of the reference display 104 when the display apparatus 306 is inserted in the recess 304 in housing 302. The radiopaque cover protects the reference display 104 from mechanical damage and the radiopaque cover protects the reference display 104 from electromagnetic damage. In some embodiments, the radiopaque cover is a leaded polycarbonate lens. In some embodiments, the translucent window 308 is a radiopaque window that provides the same functionality as the radiopaque cover.

In some embodiments of apparatus 300, an electrical interface (not shown) is mounted in one of the walls of the housing recess 302. The electrical interface is operable to mechanically and electrically integrate with a complimentary electrical interface on the outside of the display apparatus 306. Examples of complimentary electrical interface include a pair of either serial or parallel male/female electrical interfaces. The integrated electrical interface completes an electronic communication path 106 between the apparatus 300 and the display apparatus 306.

In some embodiments, housing 302 comprises another recess 310. The recess 310 has inner dimensions suitable to receive a battery 312 for powering the apparatus 300. The battery 312 is a separate apparatus from apparatus 300. In those embodiments, another electrical interface (not shown) is mounted in one of the walls of the housing recess 312. The other electrical interface is operable to mechanically and electrically integrate with a complimentary electrical interface on the outside of the battery 312.

Figure 4:
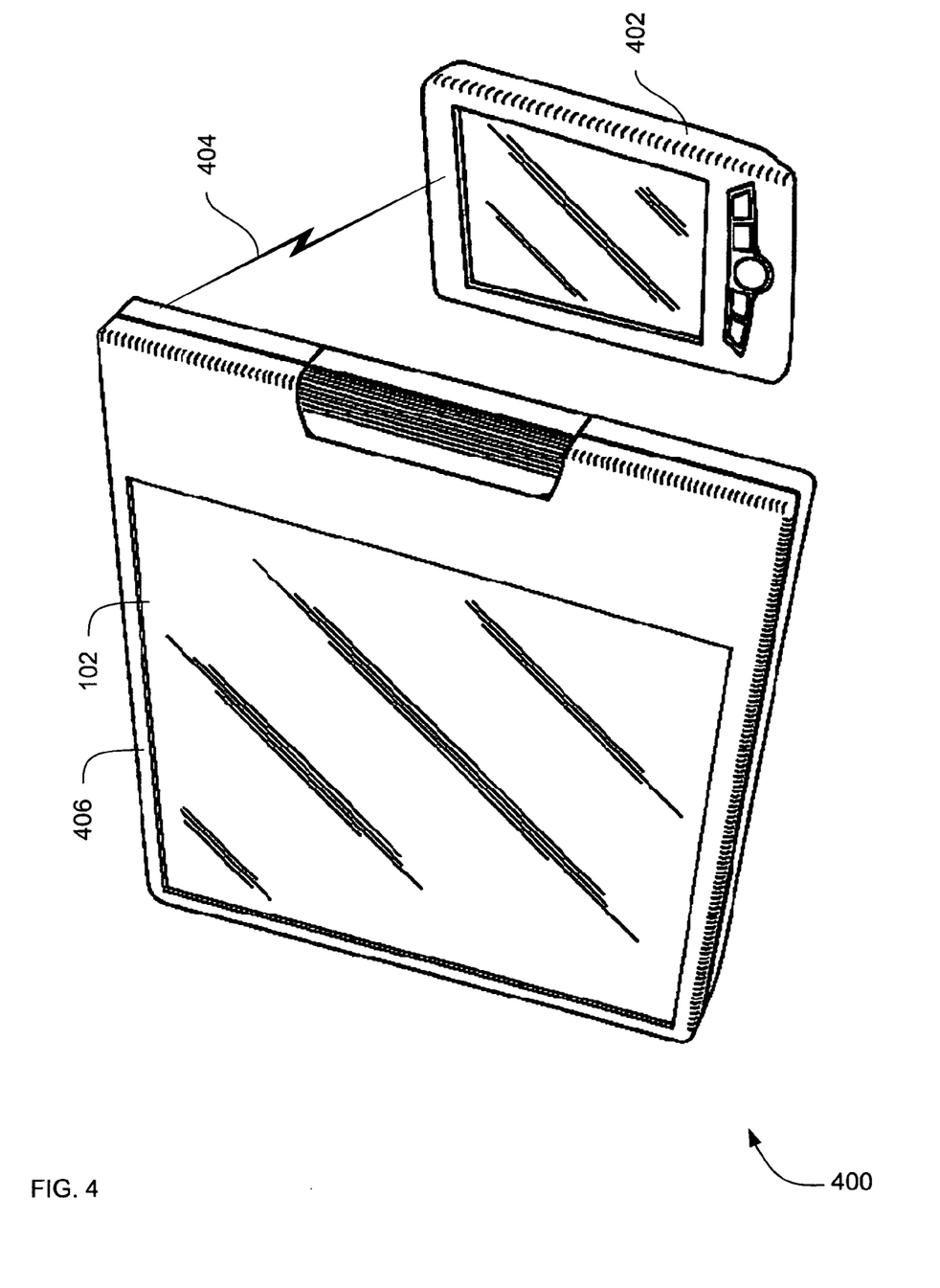
FIG. 4 is a diagram of apparatus according to an embodiment in which a reference display is operably coupled to a digital image detector through a wireless communication path.

FIG. 4 is a diagram of apparatus 400 according to an embodiment in which a reference display is operably coupled to a digital image detector through a wireless communication path.

Apparatus 400 includes a transceiver that communicates with a personal digital assistant (PDA) 402 or other handheld electronic device. The PDA has connectivity to a wireless communication path 404, through which the PDA 402 communicates to the digital image detector 406 that includes a digital image receptor 102. The digital image detector 406 communicates to the wireless communication path 404 through a wireless transceiver (not shown) housed within the digital image detector 406.

FIG. 5 is a diagram of a reference display 500 according to an embodiment. Apparatus 500 solves the need in the art to provide reference information on an imaging procedure.

Reference display 500 includes a visual display 502, such as a color liquid crystal diode (LCD) screen or other electronic display. The dimensions of the visual display 502 vary in different embodiments, but some exemplary dimensions are 3×3", 3¾×2¼" and the dimensions of a conventional computer monitor such as 13" diagonal, 14" diagonal, 15" diagonal or 19" diagonal.

Reference information is displayed on the visual display 502. Examples of reference information include a reference image 504 and textual information such as patient identification 506, attending physician 508, procedure technique 510, battery state 512, communication state 514, image registration 516, procedure technique parameters 518, service tool/diagnostic 520 and pager 522 information. In some embodiments the reference image 504 is displayed in the background to the other information. The position of the information on the visual display 502 in FIG. 5 is merely one possible layout. Many other layouts and positions of the information are possible.

The reference image 504 is a smaller, lower resolution version of an image captured by a digital image detector, such as the digital image receptor 102. The procedural technique 506 information describes the imaging technique used to capture an image on a digital image detector, such as "Kvp 100" to represent a setting of 100 kilo voltage potential on the X-ray source, "Kev 150" to represent a setting of 150 kilo electron volts, "ma 20" to represent a setting of 20 kilo amperes, and/or "mAs 10" to represent a setting of 10 milliampere seconds, used in the imaging procedure.

Figure 6:
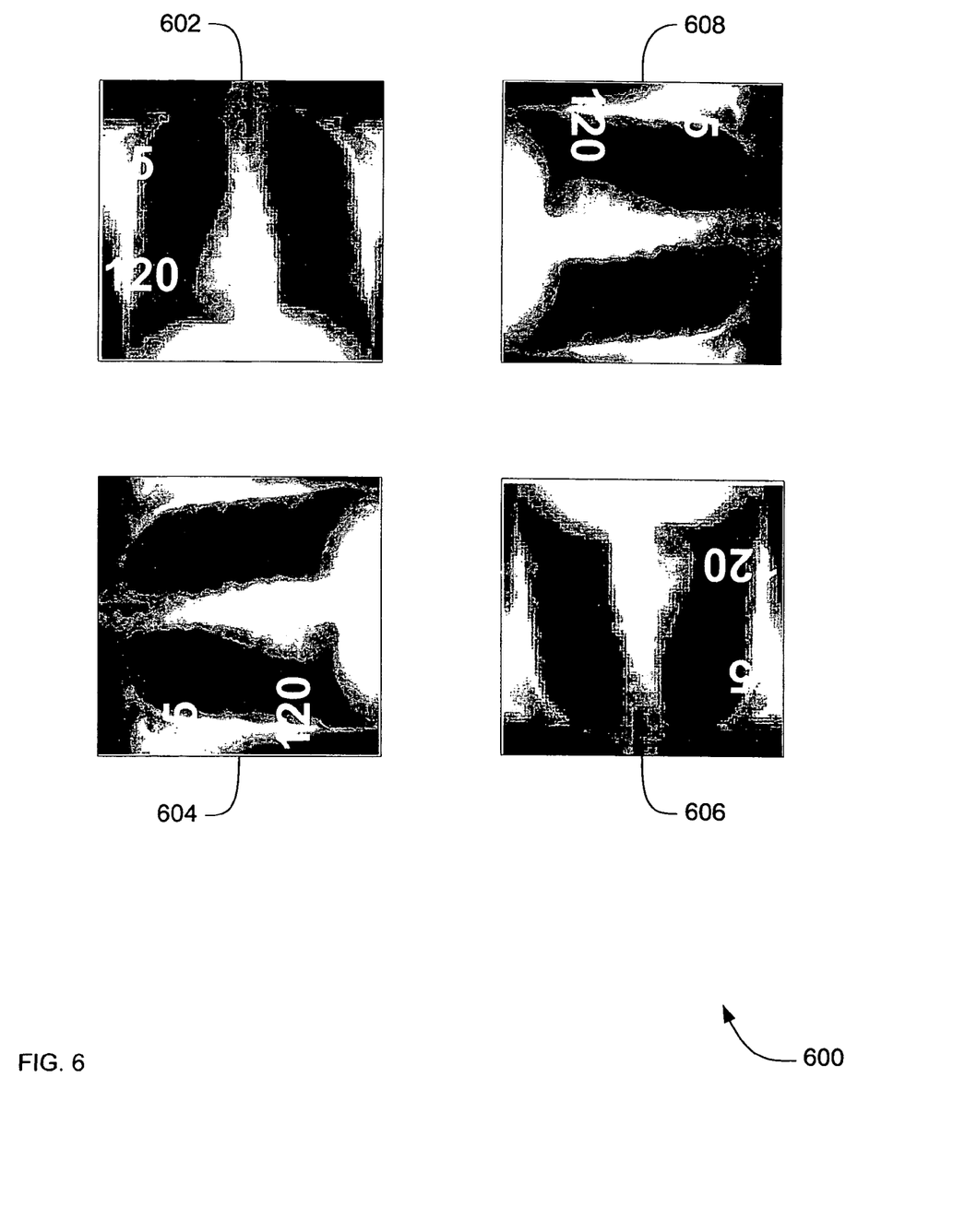
FIG. 6 is a diagram of four rotated visual displays according to an embodiment.

FIG. 6 is a diagram of four rotated visual displays 600 according to an embodiment. In some embodiments the displayed textual information is rotated in reference to the orientation of the operator, the subject of the imaging and/or the digital image detector.

Display 602 shows the orientation of the displayed textual information in a top-down, left-right orientation. Display 604 shows the displayed textual information rotated 90 degrees to the left. Display 604 shows the display rotated 180 degrees. Display 604 shows the displayed textual information rotated 90 degrees to the right. However, the displayed textual information can rotated any number of degrees to be readable in reference to the orientation of the operator, the subject of the imaging and/or the digital image detector.

Figure 7:
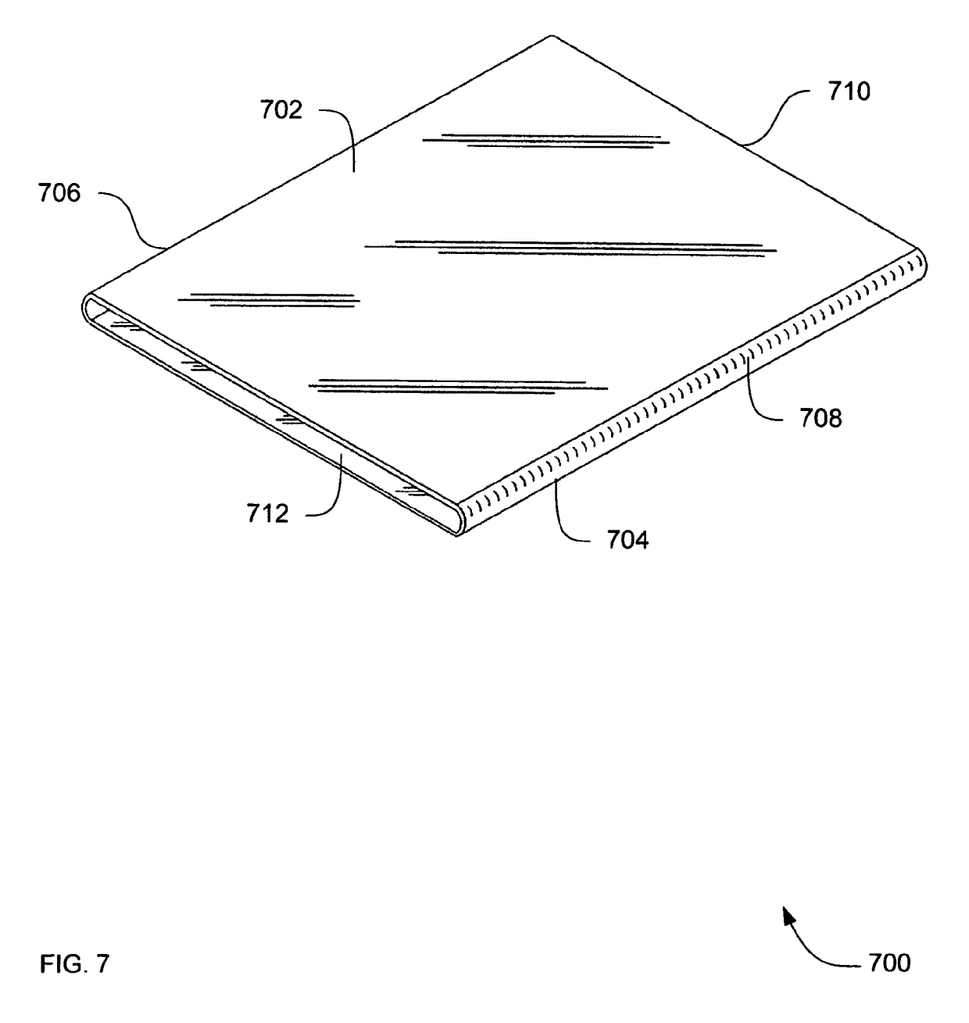
FIG. 7 is a three dimensional perspective of a radiolucent sleeve for a digital image detector according to an embodiment.

FIG. 7 is a three dimensional perspective of a radiolucent sleeve 700 for a digital image detector according to an embodiment. Apparatus 700 solves the need in the art to protect the exterior housing of digital image receptors from damage by contact from other objects.

The radiolucent sleeve 700 includes a front 702, a back, 704, two sides 706 and 708 and closed end 710. A digital image detector, such as apparatus 200, 300 and 400, is inserted in an open end 712. The radiolucent sleeve 700 protects the exterior housing of digital image receptors from damage by contact from other objects. The radiolucent characteristics allow electromagnetic energy to pass through the radiolucent sleeve 700 so that a digital image receptor inserted into the radiolucent sleeve 700 may operate while in the radiolucent sleeve 700.

In some embodiments, the radiolucent sleeve 700 includes the radiolucent material graphite.

In some embodiments, an inner circumference formed by the front, the two sides, the back and the closed end of the radiolucent sleeve is about equal to the outer circumference of the digital image detector. In some further embodiments, the inner circumference is about equal to the outer circumference of the digital image detector to the extent that the radiolucent sleeve has a snug fit when the digital image detector is placed within the radiolucent sleeve.

Figure 8:
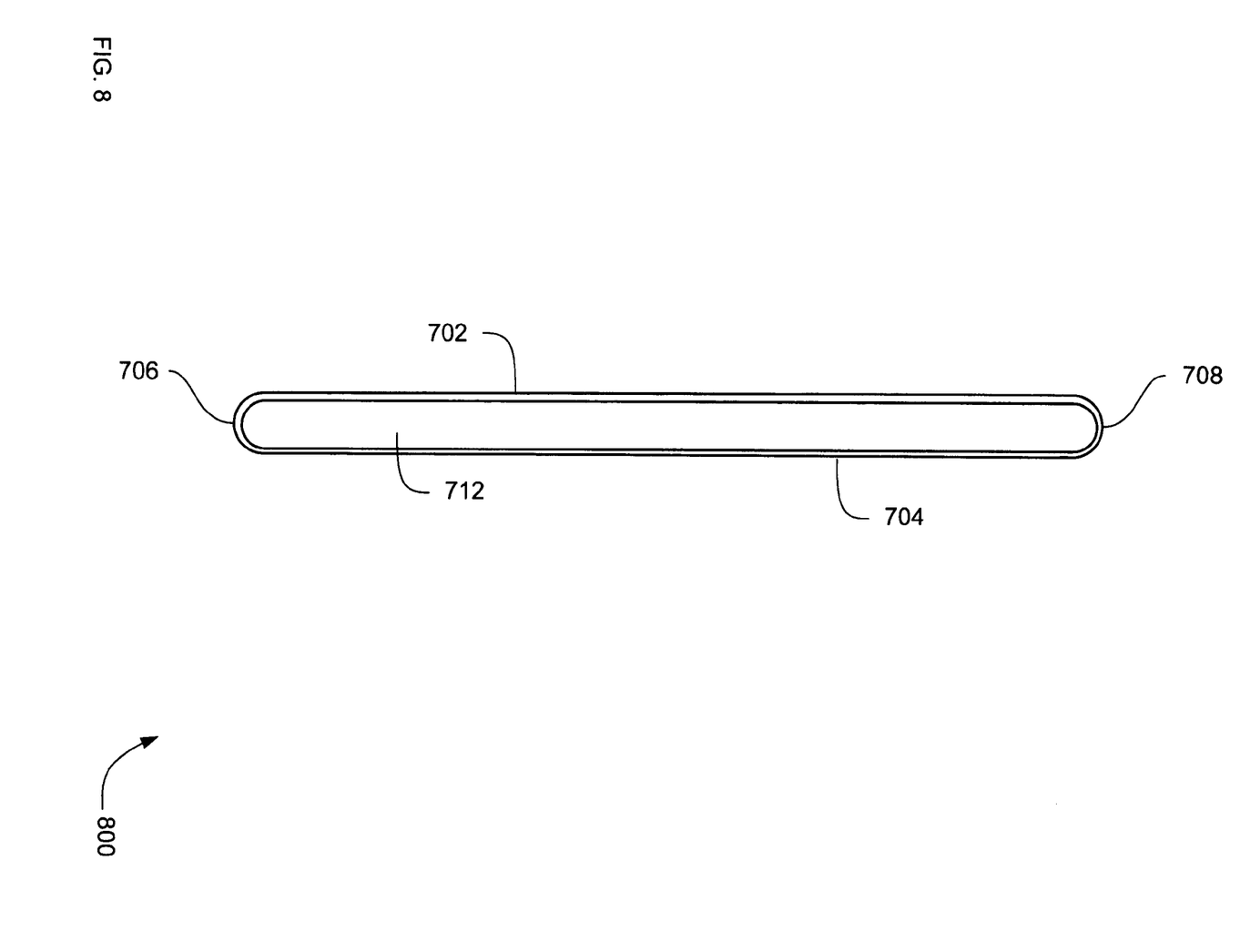
FIG. 8 is a diagram of a top-view of the radiolucent sleeve.

FIG. 8 is a diagram of a top-view 800 of the radiolucent sleeve 700.

Figure 9:
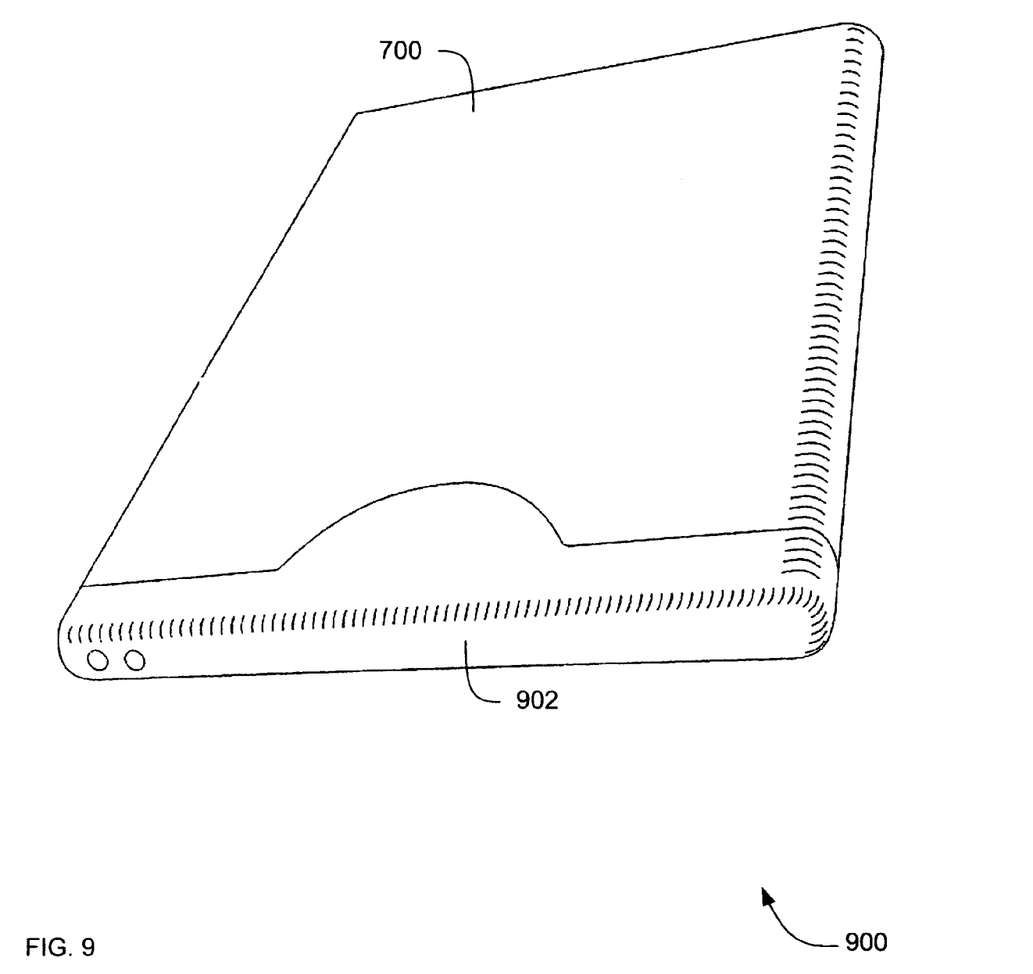
FIG. 9 is a three dimensional perspective of a radiolucent sleeve containing a digital image detector according to an embodiment.

FIG. 9 is a three dimensional perspective of a radiolucent sleeve 700 containing a digital image detector 902 according to an embodiment.

Methods of an Embodiment

In the previous section, apparatus of the operation of an embodiment was described. In this section, the particular methods performed by a reference display of such an embodiment are described by reference to a series of flowcharts.

Figure 10:
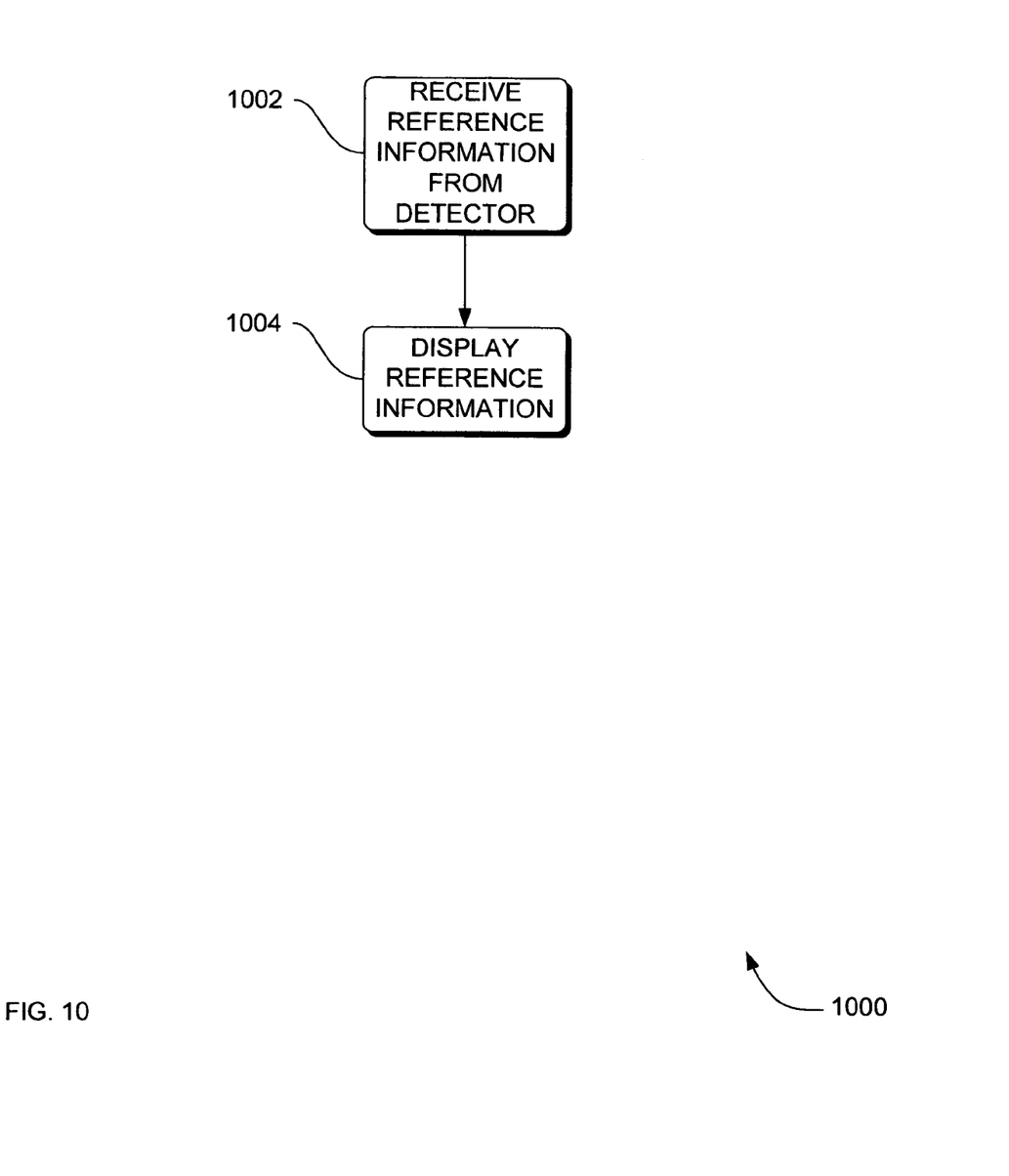
FIG. 10 is a flowchart of a method according to an embodiment.

FIG. 10 is a flowchart of a method 1000 of communication between a digital image receptor and a reference display according to an embodiment. Method 1000 solves the need in the art for improved access to the imaging information by the operator and the need in the art for improved access to the imaging information by a human subject of the imaging procedure. Method 1000 is performed by a reference display 104 in FIGS. 1-6.

Method 1000 includes receiving 1002 reference information from a digital image receptor 102 through a communication path 106. Method 1000 also includes displaying 1004 the reference information.

Figure 11:
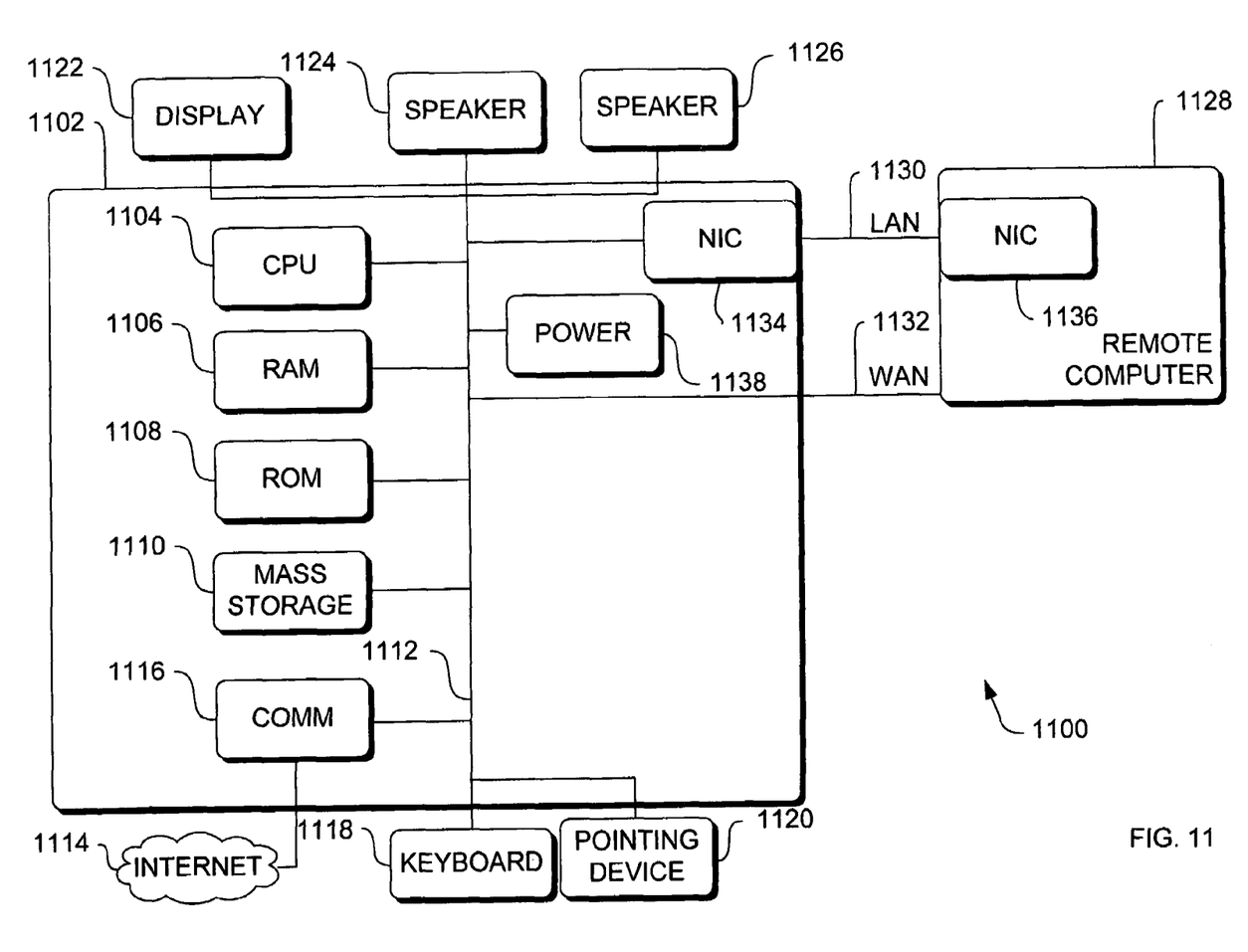
FIG. 11 is a block diagram of the hardware and operating environment in which different embodiments can be practiced.

In some embodiments, method 1000 is implemented as a computer data signal embodied in a carrier wave, that represents a sequence of instructions which, when executed by a processor, such as processor 1104 in FIG. 1100, cause the processor to perform the respective method. In other embodiments, method 1000 is implemented as a computer-accessible medium having executable instructions capable of directing a processor, such as processor 1104 in FIG. 1100, to perform the respective method. In varying embodiments, the medium is a magnetic medium, an electronic medium, or an optical medium.

Hardware and Operating Environment

FIG. 11 is a block diagram of the hardware and operating environment 1100 in which different embodiments can be practiced. The description of FIG. 11 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

Computer 1102 includes a processor 1104, commercially available from Intel, Motorola, Cyrix and others. Computer 1102 also includes random-access memory (RAM) 1106, read-only memory (ROM) 1108, and one or more mass storage devices 1110, and a system bus 1112, that operatively couples various system components to the processing unit 1104. The memory 1106, 1108, and mass storage devices, 1110, are types of computer-accessible media. Mass storage devices 1110 are more specifically types of nonvolatile computer-accessible media and can include one or more hard disk drives, floppy disk drives, optical disk drives, and tape cartridge drives. The processor 1104 executes computer programs stored on the computer-accessible media.

Computer 1102 can be communicatively connected to the Internet 1114 via a communication device 1116. Internet 1114 connectivity is well known within the art. In one embodiment, a communication device 1116 is a modem that responds to communication drivers to connect to the Internet via what is known in the art as a "dial-up connection." In another embodiment, a communication device 1116 is an Ethernet® or similar hardware network card connected to a local-area network (LAN) that itself is connected to the Internet via what is known in the art as a "direct connection" (e.g., T1 line, etc.).

A user enters commands and information into the computer 1102 through input devices such as a keyboard 1118 or a pointing device 1120. The keyboard 1118 permits entry of textual information into computer 1102, as known within the art, and embodiments are not limited to any particular type of keyboard. Pointing device 1120 permits the control of the screen pointer provided by a graphical user interface (GUI) of operating systems such as versions of Microsoft Windows®. Embodiments are not limited to any particular pointing device 1120. Such pointing devices include mice, touch pads, trackballs, remote controls and point sticks. Other input devices (not shown) can include a microphone, joystick, game pad, satellite dish, scanner, or the like.

In some embodiments, computer 1102 is operatively coupled to a display device 1122. Display device 1122 is connected to the system bus 1112. Display device 1122 permits the display of information, including computer, video and other information, for viewing by a user of the computer. Embodiments are not limited to any particular display device 1122. Such display devices include cathode ray tube (CRT) displays (monitors), as well as flat panel displays such as liquid crystal displays (LCD's). In addition to a monitor, computers typically include other peripheral input/output devices such as printers (not shown). Speakers 1124 and 1126 provide audio output of signals. Speakers 1124 and 1126 are also connected to the system bus 1112.

Computer 1102 also includes an operating system (not shown) that is stored on the computer-accessible media RAM 1106, ROM 1108, and mass storage device 1110, and is and executed by the processor 1104. Examples of operating systems include Microsoft Windows®, Apple MacOS®, Linux®, UNIX®. Examples are not limited to any particular operating system, however, and the construction and use of such operating systems are well known within the art.

Embodiments of computer 1102 are not limited to any type of computer 1102. In varying embodiments, computer 1102 comprises a PC-compatible computer, a MacOS®-compatible computer, a Linux®-compatible computer, or a UNIX®-compatible computer. The construction and operation of such computers are well known within the art.

Computer 1102 can be operated using at least one operating system to provide a graphical user interface (GUI) including a user-controllable pointer. Computer 1102 can have at least one web browser application program executing within at least one operating system, to permit users of computer 1102 to access intranet or Internet world-wide-web pages as addressed by Universal Resource Locator (URL) addresses. Examples of browser application programs include Netscape Navigator® and Microsoft Internet Explorer®.

The computer 1102 can operate in a networked environment using logical connections to one or more remote computers, such as remote computer 1128. These logical connections are achieved by a communication device coupled to, or a part of, the computer 1102. Embodiments are not limited to a particular type of communications device. The remote computer 1128 can be another computer, a server, a router, a network PC, a client, a peer device or other common network node. The logical connections depicted in FIG. 11 include a local-area network (LAN)

1130 and a wide-area network (WAN) 1132. Such networking environments are commonplace in offices, enterprise-wide computer networks, intranets and the Internet.

When used in a LAN-networking environment, the computer 1102 and remote computer 1128 are connected to the local network 1130 through network interfaces or adapters 1134, which is one type of communications device 1116. Remote computer 1128 also includes a network device 1136. When used in a conventional WAN-networking environment, the computer 1102 and remote computer 1128 communicate with a WAN 1132 through modems (not shown). The modem, which can be internal or external, is connected to the system bus 1112. In a networked environment, program modules depicted relative to the computer 1102, or portions thereof, can be stored in the remote computer 1128.

Computer 1102 also includes power supply 1138. Each power supply can be a battery.

CONCLUSION

An integrated reference display for digital image detectors has been described. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations. For example, although described in functional terms, one of ordinary skill in the art will appreciate that implementations can be made in object-oriented design or any other design that provides the required function.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future digital image detector and receptors and PDA devices.

The integration of reference display on/in a digital detector enhances the functionality of the device by providing a convenient opportunity to check anatomical alignment as well as technique parameters that were the basis for the image capture. This functionality will enhance user confidence and improve procedural flow/thru-put.

The integration of a reference display on/in the digital detector provides rapid assessment of the desired outcome of the procedure reducing repositioning and retakes. The integration of the reference display also demystifies the technology in the patient experience.

The terminology used in this application with respect to communication is meant to include all communication environments and alternate technologies which provide the same functionality as described herein.

We claim:

1. A system to image a subject, the system comprising:
   a digital image detector having a side;
   a digital image receptor mounted in the side of the digital image detector; and
   a reference display mounted in the side of the digital image detector.

2. The system of claim 1, wherein the side further comprises:
   a front side.

3. The system of claim 1, wherein the reference display further comprises:
   a reference display removably mounted in the digital image detector.

4. The system of claim 1, wherein the digital image detector further comprises:
   a medical digital X-ray image detector.

5. The system of claim 1, wherein the digital image detector further comprises:
   a medical digital image detector.

6. The system of claim 1, wherein the reference display further comprises:
   a color liquid crystal display.

7. The system of claim 1, wherein the reference display further comprises:
   a reference display having physical dimensions no greater than three inches in any direction.

8. The system of claim 1, wherein the reference display further comprises:
   a reference display operable to display information selected from the group consisting of:
   a reference image, patient identification, attending physician, procedure technique, battery state, communication state, image registration, procedure technique parameters, service tool/diagnostic information and pager information.

9. The system of claim 1, wherein the system further comprises:
   a radiopaque cover attached to the system that is moveable over the reference display.

10. An apparatus to image a human medical patient, the apparatus comprising:
    a medical X-ray digital image detector having a side; and
    a reference display removeably mounted in the side of the medical X-ray digital image detector,
    wherein the reference display further comprises:
    a color liquid crystal display comprising physical dimensions no greater than three inches in any direction.

11. The apparatus of claim 10, wherein the reference display further comprises:
    a reference display fixedly mounted in the digital image detector.

12. The apparatus of claim 10, wherein the reference display further comprises:
    a reference display removably mounted in the digital image detector.

13. The apparatus of claim 10, wherein the reference display further comprises:
    a reference display having physical dimensions no greater than three inches in any direction.

14. The apparatus of claim 10, wherein the reference display further comprises:
    a reference display located in a room as the digital image detector.

15. The apparatus of claim 10, wherein the reference display further comprises:
    a reference display operable to display information selected from the group consisting of:
    a reference image, patient identification, attending physician, procedure technique, battery state, communication state, image registration, procedure technique parameters, service tool/diagnostic information and pager information.

16. The apparatus of claim 15, wherein the procedure technique, battery state, communication state, image registration, patient identification, attending physician, procedure technique parameters, service tool/diagnostic information and pager information further consists of textual information, and the reference display is operable to display the textual information rotated at an orientation selected from 90 degrees, 180 degrees and 270 degrees to the left.

17. The apparatus of claim 10, wherein the apparatus further comprises:
a radiopaque cover attached to the apparatus that is moveable over the reference display.

18. A medical digital image detector to image a subject, the medical digital image detector comprising:
a housing comprising a recess in a side, the recess having inner dimensions suitable to receive a reference display; and
a digital image receptor mounted in the side of the housing, and operably coupled to an interface, the interface operable to couple the interface to the reference display.

19. The medical digital image detector of claim 18, wherein the interface further comprises:
an electrical interface mounted in a wall of the recess of the housing operable to integrate with a complimentary interface of the reference display.

20. The medical digital image detector of claim 18, wherein the medical digital image detector further comprises:
a radiopaque cover attached to the medical digital image detector that is moveable over the reference display.

21. The medical digital image detector of claim 18, wherein the interface further comprises:
a wireless transceiver in the housing.

22. The medical digital image detector of claim 18, wherein the reference display further comprises:
a reference display fixedly mounted in the medical digital image detector.

23. The medical digital image detector of claim 22, wherein the reference display further comprises:
a color liquid crystal display.

24. The medical digital image detector of claim 22, wherein the reference display further comprises:
a reference display having physical dimensions no greater than three inches in any direction.

25. A medical X-ray digital image detector to display an image of a subject, the medical X-ray digital image detector comprising:
a housing having outer walls, the outer walls comprising dimensions suitable to fit a X-ray digital image receptor within a recess of the housing;
an electronic display mounted in the housing; and
an electrical interface mounted in one of the outer walls of the housing operable to integrate with a .complimentary electrical interface, the electrical interface operably coupled to the electronic display.

26. A medical digital image detector comprising: a housing having a side;
a medical X-ray digital image receptor mounted in the side of the housing; and
a reference display fixedly mounted in the side of the of the housing and operably coupled to the medical X-ray digital image receptor, the reference display further comprising:
a color liquid crystal display comprising physical dimensions no greater than three inches in any direction, the color liquid crystal display visible outside the housing wherein the reference display is operable to:
receive reference information from the digital image receptor through a communication path;
display the reference information.

27. The medical digital image detector of claim 26, wherein the reference information further comprises:
reference information selected from the group consisting of:
a reference image, patient identification, attending physician, procedure technique, battery state, communication state, image registration, procedure technique parameters, service tool/diagnostic information and pager information.

28. The medical digital image detector of claim 26, further comprising:
a radiopaque cover attached to the medical digital image detector that is moveable over the reference display.

29. The medical digital image detector of claim 26, further comprising:
at least one status light mounted on a surface of the housing.

30. A medical digital image detector comprising:
a housing having a side;
a medical X-ray digital image receptor mounted in the side of the housing; and
a reference display removably mounted in the side of the housing and operable to couple to the medical X-ray digital image receptor, the reference display further comprising:
a color liquid crystal display comprising physical dimensions no greater than three inches in any direction,
wherein the reference display is operable to:
receive reference information from the digital image receptor through a communication path;
display the reference information.

31. The medical digital image detector of claim 30, wherein the reference information further comprises:
reference information selected from the group consisting of:
a reference image, patient identification, attending physician, procedure technique, battery state, communication state, image registration, procedure technique parameters, service tool/diagnostic information and pager information.

32. The medical digital image detector of claim 30, wherein the medical digital image detector further comprises:
a radiopaque cover attached to the medical digital image detector that is moveable over the reference display.

33. The medical digital image detector of claim 30, further comprising:
at least one status light mounted on a surface of the housing.

34. A medical digital image detector comprising:
a housing having a side;
a reference display mounted in the side of the housing;
a medical X-ray digital image receptor mounted in the side of the housing; and
a transceiver mounted in the housing and operably coupled to the medical X-ray digital image receptor and operably coupled to the reference display, the transceiver operable to transmit reference information to through a wirelesss communication path.

35. The medical digital image detector of claim 34, wherein the reference information further comprises:

reference information selected from the group consisting of:
a reference image, patient identification, attending physician, procedure technique, battery state, communication state, image registration, procedure technique parameters, service tool/diagnostic information and pager information.

36. A reference display comprising:

an electrical interface operable to couple with a complimentary electrical interface of a medical digital image detector on the same side of a digital image receptor of the medical digital image detector; and a color liquid crystal display comprising physical dimensions no greater than three inches in any direction, the color liquid crystal display being operably coupled to the electrical interface wherein the color liquid crystal display is operable to display medical reference information selected from the group consisting of:

a reference image, patient identification, attending physician, procedure technique, battery state, communication state, image registration, procedure technique parameters, service tool/diagnostic information and pager information.

37. The reference display of claim 36, wherein the reference display is operable to:

receive reference information from the digital image detector through the communication path; and display the reference information.

38. The reference display of claim 37, wherein the communication path further comprises:

a wireless communication path.

* * * * *